US012774539B2

(12) United States Patent
Gregoris et al.

(10) Patent No.: US 12,774,539 B2
(45) Date of Patent: Oct. 27, 2026

(54) METHOD AND APPARATUS FOR PRODUCING A COSMETIC PRODUCT

(71) Applicant: BAKEL S.R.L., Udine (IT)

(72) Inventors: Raffaella Gregoris, Udine (IT); Stefano Manfredini, Vigarano Mainarda (IT); Silvia Vertuani, Ferrara (IT); Martina Roso, Verona (IT)

(73) Assignee: BAKEL S.R.L., Udine (IT)

(*) Notice: Subject to any disclaimer, the term of this patent is extended or adjusted under 35 U.S.C. 154(b) by 631 days.

(21) Appl. No.: 17/798,002

(22) PCT Filed: Feb. 12, 2021

(86) PCT No.: PCT/IB2021/051194
§ 371 (c)(1),
(2) Date: Aug. 5, 2022

(87) PCT Pub. No.: WO2021/161254
PCT Pub. Date: Aug. 19, 2021

(65) Prior Publication Data

US 2023/0059989 A1 Feb. 23, 2023

(30) Foreign Application Priority Data

Feb. 13, 2020 (IT) ........................ 102020000002839

(51) Int. Cl.
*D01D 5/00* (2006.01)
*A61K 8/02* (2006.01)
(Continued)

(52) U.S. Cl.
CPC ......... *D01D 5/0084* (2013.01); *A61K 8/0208* (2013.01); *A61K 8/73* (2013.01);
(Continued)

(58) Field of Classification Search
CPC ........ D01D 5/0007–0092; A61K 8/735; A61K 2800/805; A61K 2800/87; A61K 8/0208;
(Continued)

(56) References Cited

U.S. PATENT DOCUMENTS 6,467,621 B1 * 10/2002 Ishida .................... A61K 9/703 206/460
6,770,286 B1 8/2004 Berry
(Continued)

FOREIGN PATENT DOCUMENTS

CN 107675359 A 2/2018
CN 109998932 A 7/2019
(Continued)

OTHER PUBLICATIONS

International Search Report from PCT/IB2021/051194 dated Jun. 8, 2021, 13 pages.

*Primary Examiner* — Jeffrey M Wollschlager
(74) *Attorney, Agent, or Firm* — Calfee, Halter & Griswold LLP

(57) ABSTRACT

The method to produce a packaged cosmetic product comprises a step of feeding a support film along a feed path, a step of forming a membrane substrate, and a step of packaging the membrane substrate. The method can be implemented by means of a suitable apparatus, which comprises a station for feeding the support film, a station for forming the membrane substrate, and a packaging unit, which are disposed in succession along the feed path of the support film.

12 Claims, 1 Drawing Sheet

(51) Int. Cl.
*A61K 8/73* (2006.01)
*A61Q 19/00* (2006.01)
*D01F 9/00* (2006.01)

(52) U.S. Cl.
CPC .............. *A61K 8/731* (2013.01); *A61K 8/733* (2013.01); *A61K 8/735* (2013.01); *A61Q 19/00* (2013.01); *D01D 5/0007* (2013.01); *D01D 5/003* (2013.01); *D01D 5/0061* (2013.01); *D01F 9/00* (2013.01); *A61K 2800/805* (2013.01); *A61K 2800/87* (2013.01)

(58) Field of Classification Search
CPC .......... A61K 8/73; A61K 8/731; A61Q 19/00; D01F 9/00
See application file for complete search history.

(56) References Cited

U.S. PATENT DOCUMENTS 11,969,317 B2* 4/2024 Locke ................. A61F 13/0213
2006/0264130 A1 11/2006 Karles
2010/0003344 A1* 1/2010 Cassin ................... A61Q 19/00 424/630
2013/0015092 A1* 1/2013 Suzuki ................... B65D 75/30 206/497
2015/0174284 A1* 6/2015 Payne ................. B32B 38/0004 604/368
2016/0024690 A1* 1/2016 Francis ................ D01D 5/0092 425/162
2017/0136157 A1* 5/2017 Sato ...................... A61L 31/041
2018/0186117 A1* 7/2018 Seo ......................... B32B 5/022
2020/0093646 A1* 3/2020 Locke ................... A61F 13/022
2020/0230290 A1* 7/2020 Sandri ..................... A61L 27/26
2022/0142820 A1* 5/2022 Delury .............. A61F 13/01012
2022/0354752 A1* 11/2022 Kannan .................. A61K 8/645

FOREIGN PATENT DOCUMENTS

EP 2079860 A2 7/2009
KR 20160070910 A 6/2016

* cited by examiner

METHOD AND APPARATUS FOR PRODUCING A COSMETIC PRODUCT

CROSS-REFERENCE TO RELATED APPLICATIONS

This application is a 371 Application of PCT/IB2021/051194, filed on Feb. 12, 2021, which claims priority to Italian Application No. 102020000002839, filed on Feb. 13, 2020, the contents of which are hereby incorporated by reference as if recited in their entirety.

FIELD OF THE INVENTION

The present invention concerns a method to produce a cosmetic product, and also the corresponding apparatus. More particularly, the invention concerns a method and an apparatus to produce a cosmetic patch product that can be absorbed by the skin and based on polymer compounds, preferably biocompatible, and packaged. The cosmetic patch product is the type that is made up of fibers, in particular nanofibers, preferably obtained by electrospinning.

BACKGROUND OF THE INVENTION

Cosmetic products to be applied directly on the skin are widely known, which are formulated in various forms compatible with the skin and/or which are absorbed by the skin, such as for example, emulsions, creams, lotions, serums, gels, powders, oils, sun milks and suchlike, or other formulations.

These products, however, can sometimes be difficult to apply on the skin, sometimes requiring prolonged application times or a prolonged massage, in order to be completely absorbed into the dermis, and sometimes leaving cosmetic residues on the fingers or hands or on any possible applicators used.

There are also cosmetic products that are applied by means of a physical support, generally fibrous, which facilitates their application on the skin, such as in particular make-up remover wipes, which are imbued with a special cleansing composition.

One disadvantage of this type of cosmetic product is that, after use, the fibrous physical support, which does not have its own cosmetic function, as well as the packaging, have to be disposed of.

Furthermore, known fibrous physical supports have a specific surface that does not allow suitable transport and release of the active ingredients.

The question also arises that, generally, cosmetic compositions for the skin, for example those to be spread, such as cream, or in general cosmetic pastes, provide to use functional compounds for the skin and compounds that are exclusively functional for the structure of the formulation.

Functional compounds for the skin are partly or completely absorbed by the skin and bring benefits to the treated parts of the body. In general, this type of compound represents the so-called active ingredients.

The compounds that are exclusively functional for the structure of the formulation contribute to obtaining the cosmetic composition, whether it be an emulsion, a serum, or fluid, an oleolyte, a water, or a gel.

The effects of a compound that is exclusively functional for the structure of the formulation may affect the storage method, or the consistency of the cosmetic composition before its use and/or at the time of use, therefore when it is spread on the skin to be treated.

For example, a compound that is exclusively functional for the structure of the formulation can make the cosmetic composition soft, fluid or viscous; it allows to obtain a gel, prevent the separation of the oily compounds from the aqueous ones in an emulsion. Furthermore, compounds that are exclusively functional for the structure of the formulation allow to preserve the cosmetic composition, especially in the presence of water.

However, the problem arises that numerous compounds used, since they are functional for the structure of the formulation, do not bring any benefit to the skin, and indeed can even lead to a further deterioration of the treated skin. In fact, some of the compounds that are exclusively functional for the structure of the formulation remain indifferent to the skin, or they can cause, for example, further drying, pore closure, or development of allergies, dermatitis, or suchlike.

Among the compounds that are exclusively functional for the structure of the formulation, we can identify, for example, silicones, petrolatums (for example paraffin), alcohols, perfumes, stabilizers, preservatives, emulsifiers, the main function of which is to give the formulation of the cosmetic composition a "silk effect" consistency in contact with the skin and/or to give stability to the oily parts, or to increase the viscosity of gel formulations and/or increase the emollient and humectant effect of the emulsions.

For example, one problem that arises with these compounds exclusively functional for the structure of the formulation is the lack of skin compatibility, preventing the skin from breathing, also leading, for example, to its progressive drying, pore closure and/or greater sensitization.

It is also known that the presence of alcohols and preservatives on the one hand allow to preserve the cosmetic composition, and on the other hand increase the sensitization of the skin in developing dermatitis, allergies, or similar pathologies.

For example, document KR20160070910 describes a method and an apparatus for making a cosmetic product. The method provides to feed a support material in sheet form along a predefined path, along which there are three electrospinning devices, and to electrospin, on successive layers, three different solutions based on biocompatible polymer. It then provides to cover the electrospun layers by means of a protective sheet which is joined to the layers of electrospun material by compression. The product thus obtained, and not completely packaged, is subsequently wound around a reel. Among the solutions to be electrospun, at least one comprises a biocompatible polymer, in particular polyvinyl alcohol PVA and/or polyvinylpyrrolidone PVP and a functional substance, for example a crosslinking agent.

U.S. Pat. No. 6,770,286 discloses a method and an apparatus to make a cosmetic patch product, but in which the patch is not electrospun. Indeed, in this document two solutions of cosmetic substances are deposited on a first sheet fed from a first reel, and subsequently covered with a second sheet fed from a second reel. The combination is then compressed, heated in an oven, and subsequently the patch products are separated from the strip thus obtained. The products thus obtained are substantially ready to be marketed.

EP3549758 shows a product in sheet form comprising a layer consisting of nanofibers obtainable by electrospinning, and put in direct contact with a support layer. This document does not show a method to package the product, nor an apparatus to carry out said packaging.

One solution to the above problems, proposed by the Applicant, provides a cosmetic patch product based on a membrane substrate absorbable by the skin, which possibly also includes one or more active ingredients. In particular, the membrane substrate is made by electrospinning. Preferably, the cosmetic patch product is packaged, in order to protect its cosmetic properties.

As of today, there are no solutions, either as a method or as an apparatus, to produce the cosmetic article as above on an industrial scale.

There is therefore a need to perfect a method to produce a cosmetic product, and the corresponding apparatus, that can overcome at least one of the disadvantages of the state of the art.

In particular, one purpose of the present invention is to provide a method to produce a cosmetic product, already packaged, which is able to keep the properties of the product intact.

Another purpose of the present invention is to provide an apparatus that allows to produce the already packaged cosmetic product on an industrial scale.

The Applicant has devised, tested and embodied the present invention to overcome the shortcomings of the state of the art and to obtain these and other purposes and advantages.

SUMMARY OF THE INVENTION

The present invention is set forth and characterized in the independent claims. The dependent claims describe other characteristics of the present invention or variants to the main inventive idea.

In accordance with the above purposes, a method to produce a cosmetic product has been devised, and an apparatus for producing a cosmetic product has been realized, which overcome the limits of the state of the art and eliminate the defects present therein.

In accordance with some embodiments, a method is provided to produce a cosmetic product which provides a step of electrospinning a composition based on a biocompatible polymer material. This step gives rise to the formation of an electrospun membrane substrate, preferably made up of at least one fiber, even more preferably a nanofiber. The electrospun membrane substrate is deposited directly onto a support film fed along a feed path. The support film can be fed continuously or step-wise.

Preferably, the electrospinning step is carried out in a controlled atmosphere.

Following the electrospinning step, the method provides a step of packaging the electrospun membrane substrate obtained. In particular, it is provided that the packaging step allows to obtain the electrospun membrane substrate packed into a packaging, preferably closed, more preferably individual. The packaged product thus obtained can be marketed without further processing.

According to some embodiments, the packaging step comprises a coating step, in which a coating film is fed along the feed path as above, and is applied to the support film so as to cover the membrane substrate.

Subsequently, the packaging step provides a step of reciprocally joining the support film and the coating film. Advantageously, the two films are joined so as to form an internal space which encloses the electrospun substrate. It is preferable that the joining of the support film and the coating film is done by heat-sealing.

It should be noted that, in a favorable manner, although the coating film covers the membrane substrate, it is not joined to the latter, but only to the support film, so as not to modify or damage the membrane substrate. In particular, the coating film is not compressed onto the membrane substrate. Preferably, the heat-sealing takes place in zones in which the support film and the coating film are in reciprocal contact, that is, in zones in which there is no membrane substrate between them.

Advantageously, the support film and the coating film are heat-sealable. Preferably, they are made of polybutylene succinate adipate PBSA or polylactic acid PLA.

The method also provides, preferably, a cutting step aimed at cutting a portion of joined support film and coating film containing a cosmetic product. The support film and the coating film thus joined form a wrapping that contains the cosmetic product, which is in fact packaged.

The wrapping is made up of a support base and a coating layer, joined together. The support base is the portion of the support film that has been cut, while the coating layer is the portion of the coating film cut during the cutting step.

Favorably, the composition based on biocompatible polymer material comprises a first compound to be electrospun and a spinning promoter. The spinning promoter has the function of facilitating the spinning of the first compound, in particular of establishing the electrospinning method so as to obtain regular fibers.

The first compound to be electrospun is a biocompatible polymer suitable to be electrospun and selected from a group consisting of a first polysaccharide, collagen, hydroxypropyl methylcellulose HPMC and their derivatives. It should be noted that the first polysaccharide is selected from polysaccharides, that is, it can be any polysaccharide whatsoever.

Preferably, the first polysaccharide of the composition is selected from hyaluronic acid HA, starch, amylose, cellulose, chitosan, glycogen, pectin and agar.

The spinning promoter is a carrier polymer, possibly also without filler, selected from a group consisting of a second polysaccharide, chemically different from the first polysaccharide, possibly in the presence of poly(oxyethylene) PEO. Favorably, the carrier polymer, possibly also without filler, is also biocompatible. As for the first polysaccharide, the second polysaccharide is selected from polysaccharides, that is, it can be any polysaccharide whatsoever, as long as it is chemically different from the first polysaccharide. With the expression "chemically different from the first polysaccharide" we mean that the first and second polysaccharide are two molecules with different chemical structures.

Preferably, the second polysaccharide of the composition is selected from alginate and pullulan.

Preferably, the electrospinning promoter is selected from pullulan and a blend of alginate with poly(oxyethylene).

According to some embodiments, the composition also comprises an active ingredient. This active ingredient can, for example, be selected from polypeptides.

One advantage of the method as above lies in the possibility of producing a cosmetic product with topical concentrations for example of hyaluronic acid much higher than those obtainable with traditional formulations. With known methods, it is practically impossible to reach high concentrations, even with hyaluronic acid, polysaccharides, collagen, hydroxypropyl methylcellulose HPMC and their low molecular weight derivatives, since the viscosity of the product increases too much and it is not possible to exceed 5-10% by weight. With the present composition, it is possible to obtain cosmetic products that allow to apply concentrations up to 50% by weight of hyaluronic acid on the skin.

According to one aspect, there is also provided an apparatus for producing a cosmetic product which comprises a station for feeding a support film, an electrospinning station and a packaging unit. Preferably, the packaging unit comprises a station for feeding a coating film and a station for reciprocally joining the support film and the coating film. These stations are disposed in succession and along a feed path of the support film.

Preferably, the apparatus also comprises a cutting station for cutting portions of joined support film and coating film which enclose a cosmetic product. The cutting station can be disposed downstream of the station for reciprocally joining the films or it can coincide with the latter. In other words, it is possible to provide that the station for reciprocally joining the films comprises a device for reciprocal joining and cutting.

The support film and the coating film are advantageously fed by means of suitable feed members, for example of the conveyor belt type. These feed members are preferably disposed in an intermediate position between the corresponding feed station of each film and the cutting station.

BRIEF DESCRIPTION OF THE DRAWINGS

These and other aspects, characteristics and advantages of the present invention will become apparent from the following description of some embodiments, given as a non-restrictive example with reference to the attached drawings wherein.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

We will now refer in detail to the possible embodiments of the invention, of which one or more examples are shown in the attached drawings. Each example is supplied by way of illustration of the invention and shall not be understood as a limitation thereof. For example, one or more characteristics shown or described insomuch as they are part of one embodiment can be varied or adopted on, or in association with, other embodiments to produce another embodiment. It is understood that the present invention shall include all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Figure 1:
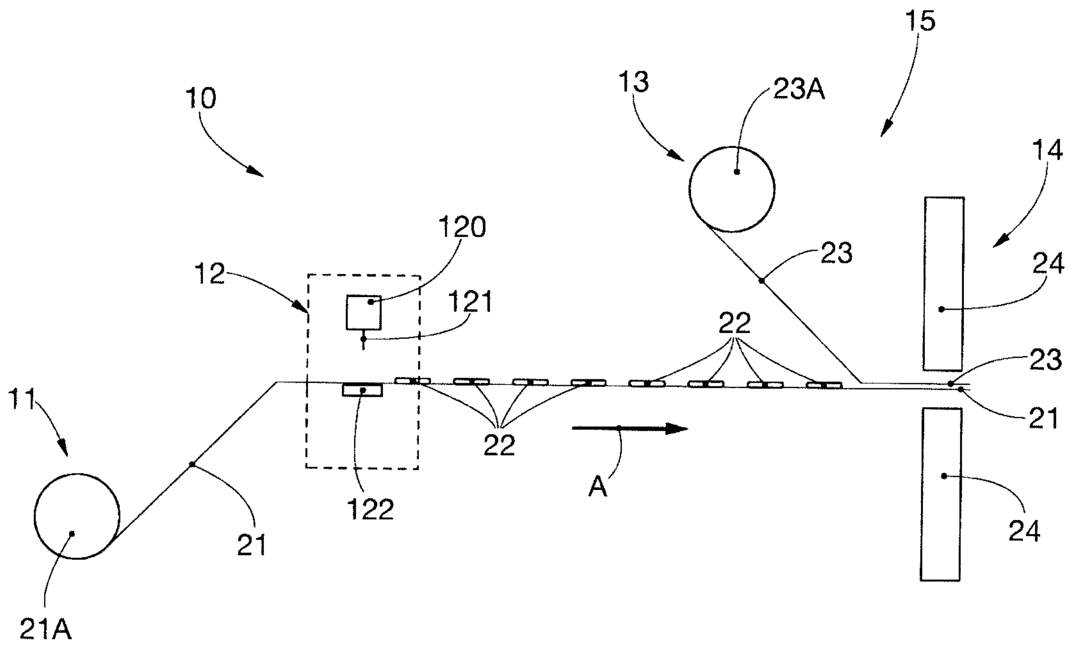
FIG. 1 is a schematic representation of an apparatus for producing a cosmetic product according to one embodiment.

FIG. 1 schematically shows an apparatus 10 for producing a packaged cosmetic product. The apparatus 10 comprises, in succession, a station 11 for feeding a support film 21, an electrospinning station 12, a station 13 for feeding a coating film 23 and a station 14 for reciprocally joining the support film 21 and the coating film 23. The station 13 for feeding the coating film 23 and the station 14 for reciprocally joining the films 21, 23 form a packaging unit 15.

Preferably, the support film 21 and the coating film 23 are made of a heat-sealable material, for example polybutylene succinate adipate PBSA or polylactic acid PLA. They can both be made with the same material or with two different materials.

In the station 11 for feeding the support film 21 there is preferably a reel 21A of support film 21. The support film 21 is fed, from the reel 21A, along a feed path, advantageously oriented in a direction of feed A. In the example shown, this direction of feed A is comprised in the plane of the sheet, it is horizontal and is oriented toward the right. However, other orientations can be provided. Conveniently, the electrospinning station 12 and the packaging unit 15, that is, the station 13 for feeding the coating film 23 and the reciprocal joining station 14, are disposed along the feed path of the support film 21.

The electrospinning station 12 comprises an electrospinning device provided, in turn, with an electrospinning head 120 provided with a corresponding delivery member 121, for example a needle. The electrospinning device also preferably comprises a collector 122 made of conductive material, for example metal, disposed facing the delivery member 121. The electrospinning device is disposed so as to have the support film 21 sliding in an intermediate position between the delivery member 121 and the collector 122, so as to deposit the electrospun fiber at exit from the delivery member 121 directly onto the support film 21. The support film 21 can slide in contact with the collector 122 or at a distance from it.

The electrospinning device 120 is of a known type, and comprises a mean for feeding a composition toward the head 120, as well as a voltage generator connected to the electrospinning head 120 and to the metal collector 122, so as to apply an electric field between the two of them. This electric field has a potential difference preferably greater than 8 kV.

In the example shown, the electrospinning head 120 is oriented so as to have the delivery member 121 in a vertical direction toward the bottom, and therefore the support film 21 underneath the head 120. In this way, in addition to the electric field, gravity is used to further aid the formation of the electrospun fiber. Alternatively, it is possible to provide that the electrospinning head 120 and the collector 122 are aligned in the horizontal direction, or in the vertical direction with the delivery member 121 oriented upward and the collector 122 above the electrospinning head 120. In such cases, the electric field has to be such as to overcome the force of gravity.

It is possible to provide a mask made of insulating material, for example of Teflon or suchlike, with apertures of controlled shape and sizes, in order to induce the deposit of the electrospun nanofiber inside predetermined areas. In this way, material waste is prevented.

Preferably, the electrospinning device is enclosed inside a hermetically closed chamber, for simplicity not shown in FIG. 1, so that the atmosphere inside it can be controlled.

In correspondence with the electrospinning station 12, an electrospun substrate 22 of the membrane type is produced, deposited directly onto the support film 21. Consequently, the electrospun substrate 22 is transported by the support film 21 along the feed path, and then through the subsequent station 13 for feeding the coating film 23, and the station 14 for reciprocally joining the films. Preferably, the electrospun substrate 22 is in the form of a non-woven fabric.

The station 13 for feeding the coating film 23 conveniently comprises a reel 23A from which the coating film 23 is fed. The reel 23A of coating film 23 is disposed at the side of the support film 21 on which the electrospun substrate 22 is deposited. The coating film 23 is then made to overlap with the support film 21 and rest on it, so as to completely cover the electrospun substrate 22.

Subsequently, the two overlapping films 21, 23 and the electrospun substrate 22 are fed together through the station 14 for reciprocally joining the films. This station conveniently comprises a device 24 for reciprocally joining the films, for example a heat-sealer of a known type.

The heat-sealer 24 preferably carries out a longitudinal seal in correspondence with the two external edges of the support 21 and coating 23 films, and at least one transverse seal of the films between two electrospun substrates 22. By longitudinal and transverse, here we mean with respect to the direction of feed A of the support film 21, as defined above. The heat-sealer can be configured to act only on the films 21, 23 to be reciprocally joined, but not on the electrospun substrate 22. For example, it can be provided to form a succession of electrospun substrates 22, as shown in the drawings, and to perform the transverse seals between two consecutive electrospun substrates 22.

Figure 2:
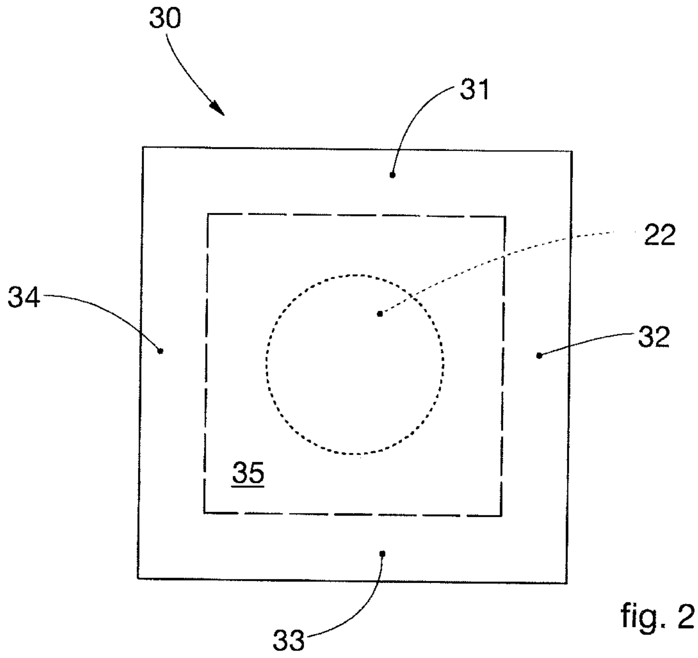
FIG. 2 is a plan view of a packaged cosmetic product obtained with the apparatus of FIG. 1.

The apparatus 10 for producing a packaged cosmetic product also preferably comprises a cutting station, in correspondence with which the reciprocally joined films 21, 23 are cut. The cut is made transversely with respect to the direction of feed A, and conveniently occurs between two electrospun substrates 22, in particular in correspondence with a transverse heat-seal. In this way, there is obtained a cosmetic product hermetically closed between a portion of support film 21 and a portion of coating film 23, the latter two portions respectively forming a support base and a coating layer of a wrapping 30 for packaging the cosmetic product, as shown in FIG. 2.

According to some embodiments, the cutting station is disposed downstream of the reciprocal joining station 14, and is therefore distinct from it. Alternatively, the cutting station can be integrated in the reciprocal joining station 14. In this case, the joining device 24 can also be a cutting device.

Conveniently, the wrapping 30 comprises four heat-seals 31, 32, 33, 34 in correspondence with its four external edges. The four heat-seals 31, 32, 33, 34 delimit a space 35 between them, created between the support base and the coating layer, inside which the cosmetic product is hermetically enclosed. Preferably, the electrospun substrate 22 is distanced from all the heat-seals 31, 32, 33, 34, that is, it is not in contact with any of them, as schematically shown in FIG. 2.

This cosmetic product favorably comprises at least one active ingredient, selected for example from peptides, amino acids, antioxidants and vitamins. The active ingredient can be integrated into the composition to be electrospun, and therefore is included in the cosmetic product right from its electrospinning, or it can be included in the membrane substrate 22 after the electrospinning. In this case, it is advisable to provide a special functionalization station, not shown in FIG. 1, disposed between the electrospinning station 12 and the station 13 for feeding the coating film 23.

According to some embodiments, the apparatus also comprises a station for stabilizing the cosmetic product, located along the feed path after the electrospinning station 12 and preferably before the station 13 for feeding the coating film 23. A treatment for stabilizing the electrospun fiber is carried out in this station, not shown, for example a heat treatment or by spraying a stabilization compound, for example a cross-linking agent, in particular if the fiber comprises alginate.

It should be noted that, preferentially, the support film 21 and the coating film 23 are fed, that is, they are moved, by means of respective feed members disposed in an intermediate position between their respective feed stations 11, 13 and the cutting station. Preferably, these feed members each comprise a conveyor belt.

According to another aspect, the invention concerns a method to produce a packaged cosmetic product. This method can be implemented by the apparatus described so far.

The method provides to feed a support film 21 along a feed path, which advantageously passes through an electrospinning station 12 and a packaging unit 15.

According to some embodiments, the packaging unit 15 comprises a station 13 for feeding a coating film 23, and a station 14 for reciprocally joining the support film 21 and the coating film 23.

In correspondence with the electrospinning station 12, a step of electrospinning a composition based on biocompatible polymer material takes place, which gives rise to the formation of at least one electrospun fiber, preferably a nanofiber. This fiber is deposited directly onto the support film 21, possibly in correspondence with one or more predetermined areas thanks to the use of a special mask of insulating material. Favorably, the electrospinning step is carried out in a controlled atmosphere, for example under controlled humidity and/or controlled temperature conditions, possibly in an inert gas atmosphere such as argon or nitrogen.

According to some embodiments, the composition based on polymer material comprises a first compound to be electrospun, which in turn comprises a biocompatible polymer suitable to be electrospun and selected from a group consisting of a first polysaccharide, collagen, hydroxypropyl methylcellulose HPMC and their derivatives. It should be noted that the first polysaccharide is selected from polysaccharides, that is, it can be any polysaccharide whatsoever.

Preferably, the first polysaccharide of the composition is selected from hyaluronic acid HA, starch, amylose, cellulose, chitosan, glycogen, pectin and agar.

According to some embodiments, the first compound to be electrospun comprises hyaluronic acid. It is possible to provide that this first compound comprises linear hyaluronic acid mixed with cross-linked hyaluronic acid. Preferably, hyaluronic acid has a molecular mass lower than 10,000 Da. This molecular weight is advantageous for the complete absorbability of the hyaluronic acid in the skin.

The composition based on biocompatible polymer material also comprises a spinning promoter, the function of which is to facilitate at least the initial spinning step of the first compound. The spinning promoter is selected from a group consisting of a second polysaccharide, chemically different from the first polysaccharide, possibly in the presence of poly(oxyethylene) PEO. Favorably, the carrier polymer without filler is also biocompatible. As for the first polysaccharide, the second polysaccharide is selected from polysaccharides, that is, it can be any polysaccharide whatsoever, as long as it is chemically different from the first polysaccharide. Preferably, the second polysaccharide of the composition is selected from alginate and pullulan.

Preferably, the electrospinning promoter is selected from pullulan and a blend of alginate with poly(oxyethylene).

The cosmetic product obtained during the electrospinning step comprises an electrospun membrane substrate, which comprises at least one fiber, preferably a nanofiber, made up of the first compound to be electrospun of the composition as above. By nanofiber we mean a fiber the diameter of which is of the order of magnitude of the nanometer, more specifically it is less than 10 μm.

After the electrospinning step, a step of packaging the product is carried out, which provides a coating step, in correspondence with the station 13 for feeding the coating film 23. In this coating step, the coating film 23 is made to overlap with the support film 21 and rest on it, on the side on which the electrospun substrate 22, formed during the previous electrospinning step, is deposited. Thus the coating film 23 completely covers the electrospun substrate 22.

There is then provided a step of reciprocally joining the support film 21 and the coating film 23, in correspondence with the reciprocal joining station 14. In this step the joining, preferably hermetic, is made so that a space is created between the two films 21, 23 in which the electrospun substrate 22 is enclosed. In other words, the two films 21, 23 are joined around the electrospun substrate 22. Preferably, the two films 21, 23 are joined longitudinally in correspondence with their longitudinal edges, and transversely in correspondence with intermediate positions between two consecutive substrates 22.

As previously mentioned, preferably the reciprocal joining of the films 21, 23 is performed by heat-sealing.

Following or at the same time as the step of joining the films 21, 23, a step of cutting the film is performed, in which a portion of joined films is separated, said portion being located between two transverse joins, or seals, and inside which an electrospun substrate 22 is enclosed This is how the packaged cosmetic product is obtained.

This packaged product is ready to be marketed, and/or stored for a predetermined amount of time, since the wrapping 30 delimits an internal space hermetically closed by the seals 31, 32, 33, 34 in which the membrane substrate 22 is contained. Advantageously, the wrapping consists of a portion of the support film 21 and a portion of the coating film 23, reciprocally joined. The portion of support film 21 forms the support base while the portion of coating film 23 forms the coating layer.

When the end user wishes to use the cosmetic product, it is sufficient to remove the coating layer, or part of it, in order to uncover the electrospun substrate 22, which is already disposed on its support base, and is therefore ready for use.

According to some embodiments, the method also comprises a step of functionalizing the membrane substrate 22, performed between the electrospinning step and the coating step, in correspondence with the functionalization station. This functionalization step provides to add at least one active ingredient, preferably selected from polypeptides, to the electrospun substrate 22.

According to some embodiments, the method also comprises a step of stabilizing the membrane substrate 22, preferably performed between the electrospinning step and the coating step, in correspondence with the stabilization station. This step provides a heat treatment of the membrane substrate, or the spraying of a stabilizing compound, which can be a cross-linking agent.

It is clear that modifications and/or additions of parts or steps may be made to the apparatus and method as described heretofore, without departing from the field and scope of the present invention as defined by the claims.

It is also clear that, although the present invention has been described with reference to some specific examples, a person of skill in the art shall certainly be able to achieve many other equivalent forms of method and apparatus for producing a cosmetic product, having the characteristics as set forth in the claims and hence all coming within the field of protection defined thereby.

In the following claims, the sole purpose of the references in brackets is to facilitate reading: they must not be considered as restrictive factors with regard to the field of protection claimed in the specific claims.

The invention claimed is:

1. A method to produce a packaged cosmetic product, comprising:

a step of feeding a support film along a feed path, a step of electrospinning a composition based on polymer and biocompatible material, in which an electrospun substrate absorbable by the skin is formed which is deposited directly on said fed support film, and a step of packaging said electrospun substrate, wherein the packaging step comprises:

a step of coating the electrospun substrate, in which a coating film is fed along the feed path and applied onto the support film so as to cover the electrospun substrate, and a step of reciprocally joining the support film and said coating film, wherein, after being deposited directly onto the support film, the electrospun substrate remains deposited on the support film and is transported by the support film along the feed path through the coating step and the reciprocally joining step, and wherein the support film and the coating film are joined around the electrospun substrate so as to enclose the electrospun substrate in a space between the support film and the coating film; and wherein the composition based on polymer and biocompatible material comprises a first compound to be electrospun and a spinning promoter, wherein the first compound to be electrospun comprises hyaluronic acid, and the spinning promoter comprises pullulan or a blend of alginate and poly(oxyethylene).

2. The method as in claim 1, wherein the step of reciprocally joining the support film and the coating film provides to join said films in zones in which these are in reciprocal contact.

3. The method as in claim 1, wherein during the step of reciprocally joining the support film and the coating film, said films are joined so as to form an internal space which encloses the electrospun substrate.

4. The method as in claim 1, comprising, after the packaging step, a cutting step in which a portion of reciprocally joined support film and coating film which enclose an electrospun substrate is cut.

5. The method as in claim 1, wherein said first compound to be electrospun further comprises at least one compound selected from a group consisting of a first polysaccharide, collagen, and hydroxypropyl methylcellulose, and said spinning promoter further comprises a second polysaccharide, chemically different from said first polysaccharide.

6. The method as in claim 1, wherein the first compound to be electrospun further comprises at least one compound selected from starch, amylose, cellulose, chitosan, glycogen, pectin and agar.

7. The method as in claim 1, wherein the first compound to be electrospun is hyaluronic acid.

8. The method as in claim 1, wherein the spinning promoter is selected from pullulan and a blend of alginate with poly(oxyethylene).

9. The method as in claim 2, wherein during the step of reciprocally joining the support film and the coating film, said films are joined so as to form an internal space which encloses the electrospun substrate.

10. The method as in claim 9, comprising, after the packaging step, a cutting step in which a portion of reciprocally joined support film and coating film which enclose an electrospun substrate is cut.

11. The method as in claim 1, wherein the support film and the coating film are made of a heat-sealable material.

12. The method as in claim 11, wherein the heat-sealable material is polybutylene succinate adipate or polylactic acid.

* * * * *